United States Patent [19]
Lin

[11] Patent Number: 6,130,040
[45] Date of Patent: Oct. 10, 2000

[54] METHOD FOR GENERATING DIRECTLY COVALENT BONDING BETWEEN INTERSTRAND NUCLEOTIDES

[76] Inventor: Shi-Lung Lin, 731 S. Chapel Ave. Apt. F, Alhambra, Calif. 91801

[21] Appl. No.: 09/004,070

[22] Filed: Jan. 8, 1998

[51] Int. Cl.[7] .............................. C12Q 1/68; C12P 19/34; C07H 19/00; C07H 21/00
[52] U.S. Cl. .......................... 435/6; 435/91.1; 435/91.2; 536/22.1; 536/25.4
[58] Field of Search ............................ 935/6, 91.1, 91.2; 536/22.1, 25.4

[56] References Cited

U.S. PATENT DOCUMENTS 5,516,663   5/1996   Backman et al. ....................... 435/91.2

OTHER PUBLICATIONS

Mar., Advanced Organic Chemistry, Third Editions, John Wiley & Sons, Inc. pp. 723 and 788, 1985.

Stratagene Catalog, p. 39, 1988.

J. M. Falleton, et al. "Phase Evaluation of Diaziquone in Childhood Cancer", 1990, pp. 167–170, Investigational New Drugs.

John A. Hartley, "DNA Cross–Linking and Sequence Selectivity of Aziridinylbenzoquionones A Unique Reaction at 5'–Gc–3'Squences with 2, 5–Diaziriding 1–1, 4 benzoqi-unone upon Reduction", 1988 pp. 11719–11724 Biochemistry vol. 50.

Ian N. Hampson, et al. Chemical Cross Linking Subtraction (CCLS) 1992, pp 289 Nucleic Acids Research.

Bruce F. Kimler, et al. "Omibination of Aziridinylbenzo-quinone and CIS–Platinum with Radiation Therapy. . . ", 1993, pp. 445–449 J. Reshation Oncology Biology, Physics vol. 26.

Niko Lai Lisitsyn, "Cloning the Difference Between Two Complex Genomes ", Feb. 12, 1993, pp. 946 Sequence vol 259.

Charlotte. T.C. Tan, et al. "Phase I Study of Azirinylbenzo-quinone (AZQ, NSC. 182986) in Children with Cancer", 1984 Cancer Research vol. 44. pp. 831–835.

I Lse Wieland, et al. "A Method for Difference Cloning: Gene Amplification Following Subtractive Hybridization", 1990, pp. 2720–2724, PNAS vol. 87.

Ueli Gulder and Beth. J. Hoffman, "A Simple and Very Efficient Method for Generating cDNA Libraries," 1983; Gene vol. 83 pp. 263–269.

*Primary Examiner*—Jezia Riley
*Attorney, Agent, or Firm*—Raymond Y. Chan; David and Raymond

[57] ABSTRACT

The present invention provides a fast, simple and direct covalent bond formation between two strands of nucleotide sequences. Non-modified first strand nucleotide sequences are hybridized with second strand nucleotide sequences, of which certain specific base structure(s) is modified by chemical reagents in order to generate covalent bonding with the first strand. While the hybridization of these two strand nucleotide sequences generates double-stranded hybrid duplexes between their homologues, covalent bond formation occurs in the region of modified base-pairs. Since neither a polymerase chain restriction nor a restriction enzyme digestion can be performed with the covalently bonded hybrid duplexes, the present invention can be used to subtract common sequences during subtractive hybridization, to inhibit nonspecific contamination during subcloning and to increase binding stability of antisense probes during in situ hybridization as well as gene therapy.

49 Claims, 2 Drawing Sheets

1  2  3  4  5  6  7  8  9

METHOD FOR GENERATING DIRECTLY COVALENT BONDING BETWEEN INTERSTRAND NUCLEOTIDES

BACKGROUND OF THE INVENTION

1. Field of the Invention

The present invention generally relates to the field of methods for generating covalently interstrand bonding between nucleotides. More particularly, the present invention relates to the field of improved methods of directly covalent bond formation between homologous nucleotide sequences.

2. Description of the Prior Art

The following references are pertinent to this invention:
1. Falletta et.al., "Phase 1 Evaluation of Diaziquone in Childhood Cancer", *Investigational New Drugs* 8: 167–170 (1990).
2. Hartley et.al., "DNA Cross-linking and Sequence Selectivity of Aziridinylbenzoquinones", *Biochemistry* 30: 11719–11724 (1991).
3. Hampson et.al., "Chemical Crosslinking Subtraction; A New Method for the Generation of subtractive hybridization probes", *Nucleic Acids Res.* 20: 2899 (1992).
4. Kimler et.al., "Combination of Aziridinylbenzoquinone and Cis-platinum with Radiation Therapy in the 9L Rat Brain Tumor Model", *International Journal of Radiation Oncology, Biology, Physics* 26: 445–450 (1993).
5. Lehninger et.al., *"Principles of Biochemistry, 2nd Edition"*, Worth Press, pp342–343 (1993).
6. Lisitsyn et.al., "Cloning the Differences Between Two Complex Genomes", *Science* 259: 946–951 (1993).
7. Sambrook et.al., *"Molecular Cloning, 2nd Edition"*, Cold Spring Harbor Laboratory Press, p10.45 (1989).
8. Solomons et.al., *"Organic Chemistry, 6th Edition"*, John Wiley & Sons Press, pp 693, 803–804 (1996).
9. Tan et.al., "Phase 1 Study of Azinridinylbenzoquinone in Children with Cancer", *Cancer Research* 44: 831–835 (1984).
10. Wicland et.al., "A Method for Difference Cloning; Gene Amplification Following Subtractive Hybridization", *Proc. Natl. Acad. Sci. USA* 87: 2720–2724 (1990).
11. Ueli et.al., "A Simple and Very Efficient Method for Generating cDNA Libraries", *Gene,* 25: pp263–269 (1983).
12. U.S. Pat. No. 5,589,339 issued to Hampson.
13. U.S. Pat. No. 5,591,575 issued to Hampson.

The ability to form covalent bonding between two nucleotide sequences has permitted a complete subtraction of common sequences during subtractive hybridization as well as a fully stable probing activity during in-situ-hybridization and antisense therapy. Because the covalent bonding is one of the strongest and most heat-stable interactions between molecules, the covalent bonding between two nucleotide sequences can sustain some harsh procedures, such as denature, salting and enzyme digestion. Based on such property, some methods have been developed either to perform chemotherapy or to isolate specific nucleotide sequences with external cross-linking chemicals by which two nucleotide strands were indirectly bonded. One of the most commonly used cross-linking chemicals to accomplish such sequence selectivity is aziridinylbenzoquinone (AZQ)-class agent (Hartley et.al., *Biochemistry* 30: 11719–11724 (1991)), involving the cross-linking of guanine and cytosine.

AZQ-class agents have been used in the chemotherapy of some cancers, such as brain tumor in rats (Kimler et.al., *International Journal of Radiation Oncology, Biology, Physics* 26: 445–450 (1993)) and phase 1 childhood cancer in human (Falletta et.al., *Investigational New Drugs* 8: 167–170 (1990); Tan et.al., *Cancer Research* 44: 831–835 (1984)). However, although AZQ successfully raises the bonding stability of double-stranded genome and reduces the replication of cancer cells, the non-specific cross-linking feature of AZQ also causes significant toxicity to the normal cells. Since the AZQ lacks sequence-specific targeting capability in vivo, some in vitro methods have been designed to detect and isolate specific nucleotide sequences with AZQ which cross-links common sequences of two compared nucleotide libraries.

Prior art attempts at simplifying subtraction with covalent affinity, such as U.S. Pat. No. 5,589,339 and U.S. Pat. No. 5,591,575 to Hampson, also uses an AZQ interstrand cross-linking agent to covalently subtract common sequences from a tester library. In brief, this method relies upon the generation of single-stranded tester and driver libraries which contain all sense or all antisense sequences. After the tester is hybridized with the driver, resulting in hybrid duplex formation if a sequence is common to both libraries, the AZQ is added to generate externally covalent bonds between the hybrid duplexes. Because the AZQ cross-links all double-stranded sequences, this kind of covalent-bonding nature greatly increases the completion of homologue subtraction after hybridization. However, in this method, both of the initial tester and driver must be all single strands due to the interstrand cross-linking nature of the AZQ-class agents, resulting in no use of genomic DNA samples, no detection of limited initial materials and no specific-primer amplification of final results. These disadvantages cause more restrictions of sample selection, less stability of sample storage and less sensitivity of final result detection in comparison with traditional methods. Also, the determination of final desired sequences is completed by a non-specific random-primer extension reaction which lowers the specificity of final results.

In summary, it is desirable to have a fast, specific and direct covalent bonding method for subtracting common sequences in a subtractive hybridization procedure as well as for increasing probing specificity in a gene targeting system, of which the results may contribute to developing a screening method for new genes, a diagnosis for inherent problems, or a therapy for diseases.

SUMMARY OF THE INVENTION

The present invention is a novel bonding generation method which provides a fast, simple, specific and direct covalent bond formation between nucleotide homologues.

Described in detail, a preferred embodiment of the present invention method includes the following steps:
a. providing a first strand of nucleotide sequences, wherein said first strand of nucleotide sequences is not modified by amino-blocking agent in order to preserve activating amino-groups on its nucleotide base structure(s);
b. contacting said first strand of nucleotide sequences in denatured form with a second strand of denatured nucleotide sequences, wherein said second strand of denatured nucleotide sequences is single-stranded by amino-blocking agent and then modified by carboxylating agent in its nucleotide base structure(s), to form a denatured mixture; and
c. permitting said first strand and said second strand of nucleotide sequences in said denatured mixture to form double-stranded hybrid duplexes comprising covalent bonding between the activating amino-groups of said first strand and the modified carboxyl-groups of said second strand of nucleotide sequences.

The preferred embodiment of the present invention method additionally may include the pre-steps of forming double-stranded amplicon DNA of the sample, and prior to commencing the aforementioned step (a):

(1) restricting the initial nucleotide sequences with a restriction endonuclease to generate cohesive termini on both ends;

(2) ligating an adaptor to the ends of the restricted sequences for generating a complementary region of a specific primer; and (3) incubating the ligated DNA in denatured form with the specific primer under conditions sufficient to permit the template-dependent extension of the primer to thereby enrich the amount of the initial nucleotide sequences.

In one aspect of this embodiment, step (b) and (c) are repeated on said hybrid duplexes at least one once. According to another aspect of this preferred embodiment, the initial sequences are amplified, preferably, by PCR in the pre-step (3).

To increase the binding force of heterohybrid duplexes, the second strand of nucleotide sequences is preferably carboxylated on the C-4 of uracil/thymine or C-5/C-6 of pyrimidines in order to covalently bonding with the amino-groups of the first strand sequences on the C-6 of adenine or C-6/C-2 of purines respectively. Most preferably, the carboxylated group is on the C-5 of uracil which covalently bond to the C-6 amino-group of adenine. Advantageously, the covalent bonds of the heterohybrid duplexes can not be broken during amplification or cloning by which the common sequences of both compared strands can be selected out and the unique sequences of the first strand can be isolated.

To prevent the reassociation of undesired second strand sequence duplexes during hybridization, the amino-groups of the second strand sequences are blocked or removed by chemically blocking agent(s). Preferably, the blocking agent is alkaline acetic chloride reagent which converts the activating amino-groups of purines into inactive acetamido-groups for preventing hydrogen bond formation between double-stranded nucleotide sequences. Advantageously, the denatured and modified second strand sequences only covalently hybridize with the homologues of the first strand sequences under specific condition, resulting in an increase of bonding efficiency. Preferably, the specific condition is under alkaline heat-stable buffer in which the blocked amino-groups of the second strand sequences are released.

The present invention also includes a kit for performing improved directly covalent bond formation between interstrand nucleotides, comprising some or all of the following components:

a. an amino-blocking agent which makes said second strand of nucleotide sequences single-stranded;

b. a carboxylating agent which generates carboxyl-groups on the nucleotide base of said second strand of nucleotide sequences; and c. a hybridization buffer which permits said first strand and said second strand of nucleotide sequences in a denatured mixture to form directly covalent-bonded hybrid duplexes.

Preferably, the amino-blocking agent is acetic anhydride reagent or alkaline acetic chloride reagent, and the carboxylating agent is hot alkaline potassium permanganate reagent. Preferably, the hybridization buffer is alkaline N-[2-hydroxyethyl]piperazine-N'-[3-propanesulfonic acid] (EPPS) and [ethylenediamine]tetraacetic acid (EDTA) mixture buffer.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is directed to an improved methods of directly covalent bond formation between nucleotide sequences, particularly between certain specific base-pairing of two strand homologous nucleotide sequences. This method is primarily designed for quickly subtracting common sequences during subtractive hybridization, inhibiting nonspecific contamination during cloning, and increasing binding stability of antisense probes dunng in situ hybridization as well as gene therapy. The purpose of the present invention relies on the subtraction force of the covalent-bonding between homologous sequences (homologues) during a polymerase chain reaction (PCR) or cloning, resulting in no contamination of the homologues. The preferred version of the present invention is based on: single-stranding of one strand nucleotide sequences, covalent modification of the single-stranded nucleotide sequences, and hybridization of the modified nucleotide sequences with another non-modified nucleotide sequences to form directly covalent bonding in specific base-pairs. In conjunction with an adaptor-ligation and a specific amplification, a very small amount of nucleotide sequences can be used as an initial sample for this method.

As used herein, the covalent modification refers to a series of redox reactions which the capability of directly covalent bonding with non-modified nucleotide sequences is render to the modified nucleotide sequences and is generated herein by using amino-blocking reagent and carboxylating reagent. The amino-blocking reagent refers to a chemical which can block or remove the amino-group of a purine base, such as acetic anhydride and alkaline acetic chloride. And, the carboxylating reagent refers to a chemical that can generate a carboxyl-group on the base structure of modified nucleotide sequences in order to form covalent bonding with non-modified nucleotide sequences, such as hot alkaline potassium permanganate. The homologues refer to the homologous (common) sequences which are common to both populations of the modified and non-modified nucleotide sequences.

Figure 1A:
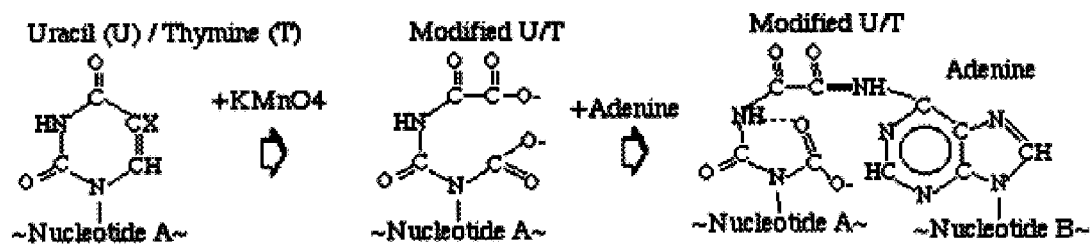
FIGS. 1($a$) and 1($b$) are illustrations of the preferred covalent modifications.
Figure 1B:
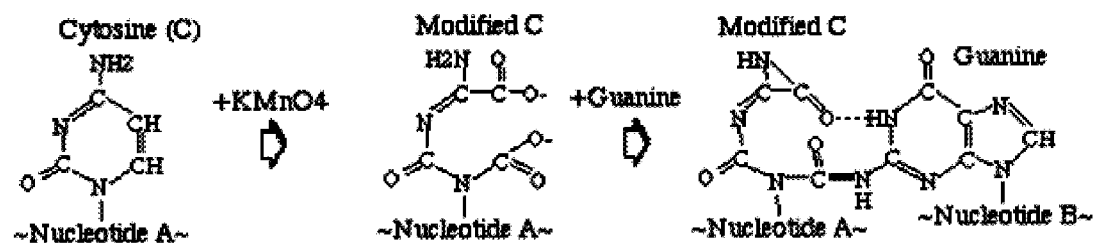

The advantages of using covalently modified nucleotide sequences are as follows: First, during hybridization, the affinity between homologues can be greatly enhanced by the covalent modification, such as the carboxyl-group on the C-5/C-6 of modified pyrimidines, resulting in peptide-bonding with the activating amino-group on the C-6/C-2 of non-modified purines respectively (FIG. 1). Such covalent peptide-bonding between homologues fully inhibit any further reaction of the homologues and therefore reduces the contamination of common nonspecific sequences. Second, the covalently modified sequences are single-stranded, resulting in high bonding efficiency of heterohybrid strand association between the modified and non-modified strand rather than between two modified strands. Third, because the covalent bonding is an internal affinity either between adenine and modified uracil or between guanine and modified cytosine, such covalent pairing feature significantly increases the specificity of covalent bonding which is generated only between sequences with highly matched base pairing.

Because the covalent modification can be greatly facilitated by using nucleotide analog-incorporated sequences, the nucleotide sequences is preferably digested by a restriction-endonuclease on both ends and ligated to a specific adaptor for incorporating nucleotide analog(s) with a template-dependent primer-extension reaction in the presence of a specific primer, preferably using a deoxyuridine triphosphate analog and the primer: SEQ ID NO. 2 5'-pCGGTAGTGACTCGGTTAAGATCGC-3'. For example, when 2'-deoxy-deoxyuridine triphosphate instead of deoxythymidine triphosphate is used to generate the modified sequences, the carboxylation reaction will occur only on the C-4 of uracil rather than the C-2 which is sometimes carboxylated if using deoxythymidine triphosphate. Preferably, here listed below are some example compounds of the incorporated analog formula:

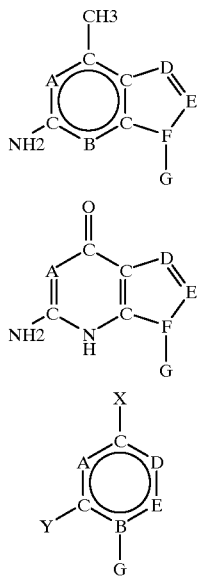

in which A, B, D, E and F are selected from either a N or a CH group, G is a 2'-deoxy-D-ribose triphosphates, and X is a methyl group while Y is a H group and vice versa. Although specially designed adaptors/primers were used to generate analog-incorporated sequences, any oligonucleotide capable of being extended into analog-incorporated sequences for the purpose of directly covalent bond formation between nucleotide homologues is within the scope of the present invention. On the other hand, when initial sample is very limited, compared non-modified nucleotide sequences will also need to be amplified by the same procedure as aforementioned but without incorporated nucleotide analog and using another primer: SEQ ID NO. 1 5'-pGCCACCAGAAGAGCGTGTACGTCC-3'.

In order to prevent the formation of covalent bonding between two modified strands, blocking the activating amino-groups of modified nucleotide sequences must be completed before covalent modification. Such blocking reaction (reduction reaction) is preferably carried out by acetylating the amino-group of purines to form an inactive acetamido-group (Solomons et. al., 1996) which is incapable of bonding to a carboxyl-group of the modified sequences, resulting in single-stranding modified sequences. Acetic anhydride and alkaline acetic chloride are major ingredients in the preferred amino-blocking reagent of the present invention. Because the single-stranded nucleotide sequences do not protect the base structure of its nucleotides from oxidative modification (oxidation reaction) any more, a carboxylating agent can easily oxidizes the alkene, carbonyl or sometimes methyl group (Solomons et.al., 1996) on the bases of the single-stranded sequences into a carboxyl-group which then forms a covalent peptide-bonding with the activating amino-group of a non-modified nucleotide sequences (redox condensing reaction). Hot alkaline potassium permanganate is a major ingredient in the preferred carboxylating reagent of the present invention based on the reaction of nucleophilic addition. Although the adenine (A), guanine (G), cytosine (C), thymine (T) and uracil (U) were used in the generation of covalently modified nucleotide sequences, any nucleotide or its analog capable of being incorporated and modified into nucleotide sequences for the purpose of directly covalent bond formation between nucleotide homologues is within the scope of the present invention. For example, such possible substitutes could be 2'-deoxy-uracil derivatives, para-toluene derivatives or else that has the same capability of being covalently modified.

After above covalent modification, the modified nucleotide sequences are then mixed with non-modified nucleotide sequences, denatured and reassociated at temperature sufficient to inhibit nonspecific hybridization, preferably between about 60–80° C., most preferably about 68–74° C. It is preferred that the amount of the modified sequences is higher than that of the non-modified sequences. In the preferred embodiment, the ratio of the modified sequences to the non-modified sequences is between 2:1 to about 30:1, most preferably about 5:1 to about 10:1. If the ratio is too high, successful enrichment of unique sequences that only exist in the non-modified sequences will not be obtained. If the ratio is too low, common nonspecific sequences will not be completely subtracted, and thus cause false-positive contamination. The optimal ratio will vary depending on the stringency of wanted covalent bonding between compared two strands of nucleotide sequences.

During the hybridization, two kinds of hybrid duplexes are formed as follows: First, homohybrid duplexes formed between two non-modified nucleotide sequences; And, heterohybrid duplexes formed between one modified and one non-modified nucleotide sequence. Because the heat-stable covalent bonding is generated only between the heterohybrid duplexes, the heterohybrid duplexes can not be amplified by a PCR or a vector-cloning in that those reactions require the separation or restriction of the nucleotide duplexes. Contrarily, the homohybrid duplexes are still formed by hydrogen-bonding which can be further treated for further reactions, such as PCR and cloning. Therefore, the present invention can be used to isolate desired unique sequences of one nucleotide library from another one by inhibiting the amplification and cloning of unwanted common sequences between them. Such isolated sequences are then used to fish out the full-length mRNA or cDNA from the nucleotide library, or to locate the isolated gene within certain chromosome by in-situ-hybridization. The information so obtained will provide further understanding of a variety of diseases, physiological phenomena, and genetic functions.

Alternatively, the present invention may be very useful in an in-situ-hybridization as well as antisense gene therapy. Because of single-stranding and resistance to restriction-enzyme digestion, if the covalently modified nucleotide sequences are labeled with terminal transferase and then used as probes in an in-situ-hybridization, the targeted nucleotides will be clearly identified in vitro or in vivo due to a stable bonding generated between the probes and the targets. In the same token, if the covalently modified nucleotide sequences are used as drugs in an antisense gene therapy, the targeted gene which we want to inactivate will be turned off in that transcription can not be accomplished though the covalent bonding region of the targeted gene. Examples as mentioned here will be developed into continuity in part of the present invention and is not intended in any way to limit the broad features or principles of the present invention.

According to the high reaction rate of covalent modifications in the preferred embodiment of the present invention, the labor- and time-consuming factors in this directly covalent bonding method can be reduced to the minimum. Also, the preparation of the covalently modified nucleotide sequences is cheaper and more efficient than that of other modified sequences in previous methods. Most importantly, such covalent modification can be carried out continuously in microtubes with only few changes of buffers. Taken together, these special features make the present invention as fast, simple, and inexpensive as a kit for specifically generate directly covalent bonding between nucleotide homologues.

Although certain preferred embodiments of the present invention have been described, the spirit and scope of the invention is by no means restricted to what is described above. For example, within the general framework of (a) one or more specific adaptors/primers for nucleotide analog-incorporation; (b) one or more nucleotide analogs incorporated into modified nucleotide sequences; (c) one or more chemical reagents which can be used to accomplish directly covalent modification; (d) one or more rounds of hybridization to complete directly covalent bond formation, there is a very large number of permutations and combinations possible, all of which are within the scope of the present invention.

EXAMPLE 1

Preparation of First and Second Strand Nucleotide Sequences

LNCaP cells, a prostate cancer cell line, were grown in DMEM medium supplemented with 2% fetal calf serum. For three-day activin treatment, 6 dishes of control cells were treated with 1.5 ml 200 ng/ml activin per day, while 4 dishes of experimental cells were not treated. On the fifth day after the first treatment, 55% reduction in growth was observed in the control cells compared to the experimental cells by both microscopy and cell counting. All cells were respectively trypsinized and total RNAs were isolated with TRIzol reagent (GIBCO/BRL). mRNAs were purified from total RNAs with a poly (oligo-dT) dextran column (Oligotex Direct Mini kit, Qiagen). After 1 μg mRNAs were mixed with an oligo-dT primer and heated to 65° C. (10 min), reverse transcription (RT) was performed with cDNA Cycle kit (Invitrogen), and all RT products (2 μg) were double-stranded with a DNA polymerase-ligase-RNase cocktail mixture (Ueli et.al., Gene, 25: pp263–269 (1983)). 1 μg of double-stranded control cDNAs were then digested by a four-cutting enzyme, such as 20U Hpa2 (5h, 37° C.), and ligated with B-specific primer: SEQ ID NO: 1 5'-pGCCACCAGAAGAGCGTGTACGTCC-3'in the 5'-end, while experimental cDNAs were ligated with A-specific primer: SEQ ID NO. 2 5'-pCGGTAGTGACTCGGTTAAGATCGC-3' in the same manner. This formed the first strand of control cDNA sequences and the second strand of experimental cDNA sequences.

EXAMPLE 2

Covalent Modification of Second Strand Nucleotide Sequences

The second strand of experimental cDNA sequences was diluted and amplified by polymerase chain reaction (PCR) with A-specific primer. During PCR, the recessed 3'-ends were filled in by Taq DNA polymerase (7 min, 72° C.) with dATP (2 mM), dCTP (2 mM), dGTP (2 mM), dTTP (0.5 mM) and dUTP (3.5 mM). Thirty cycle amplification were performed (1 min, 95° C.; 1 min, 72° C.; 3 min, 68° C.), and the amplified products, named U-DNA, were recovered by Micropure™-EZ columns (Microcon). 50 μl alkaline acetic chloride reagent was added (6 min, 98° C.) into the U-DNA of the second strand sequences to block its activating amino-groups by acetylation, by which the second strand sequences also become single-stranded. After the acetylated U-DNA was recovered by Micropure™-EZ columns and resuspended in total 10 μl 10 mM Tris-buffer (pH7.4), 40 μl alkaline potassium permanganate reagent was added (5 min, 98° C.; 30 min, 72° C.) to generate carboxyl-groups on the C-5/C-6 of uracil/cytosine which can covalently bond to the amino-groups on the C-6/C-2 of aderine/guanine of the first strand respectively. The carboxylated second strand sequences were finally recovered by Micropure™-EZ column and resuspended in total 10 μl 10 mM N,N'-diisopropylcarbodiimide N-[2-hydroxyethyl]piperazine-N'-[3-propanesulfonic acid] and [ethylenedinitrilo]tetraacetic acid (EPPS/EDTA) mixture buffer.

EXAMPLE 3

Hybridization and Specific Amplification

For hybridization, the first strand sequences (500 ng) from experimental cells was mixed with the covalently modified second strand sequences (3 μg) in EPPS/EDTA buffer and denatured at 98° C. (6 min) under alkaline condition. The mixture was then vortexed, added with 2 μl 5M NaCl to adjust salt concentration and incubated at 70° C. (20 h). The hybridized DNAs were finally diluted with 20 μl MgCl$_2$ solution (2.5 mM) and amplified by PCR with the B-specific primer. Twenty cycle amplification were performed (1 min, 95° C.; 3 min, 73° C.) after nick translation with E. coli DNA polymerase 1 plus T$_4$ DNA polymerase 3:1 mixture (5 min, 37° C. without dNTPs; 35 min, 37° C. with dNTPs), and the resulting products were phenol-extracted, isopropanol-precipitated and resuspended in 15 μl 10 mM Tris buffer for displaying on a 3% agarose gel electrophoresis (FIG. 2).

Figure 2:
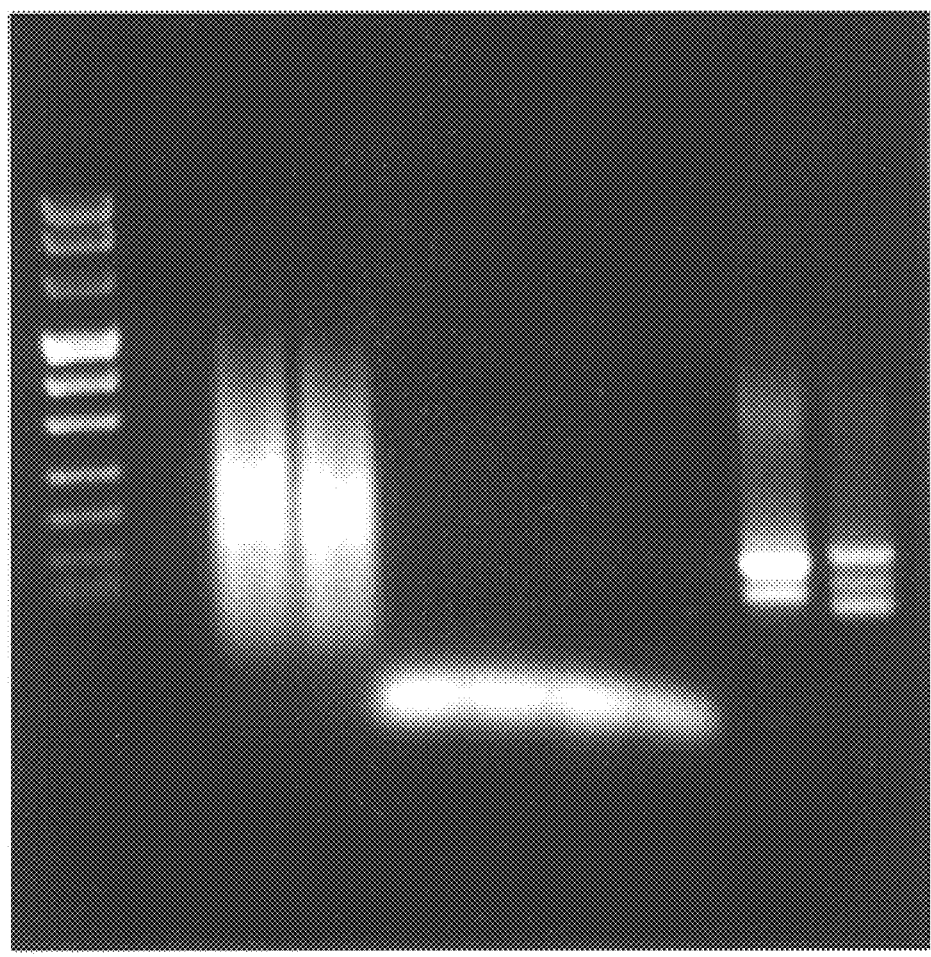
FIG. 2 illustrates the result of example 3 of the subject invention.

As shown in the FIG. 2, the first strand sequences was amplified with B-specific primer (lane 2), the second strand sequences was amplified with A-specific primer (lane 3), the first strand sequences was amplified with A-specific primer (lane 4), the second strand sequences was amplified with A-specific primer (lane 5), the first strand sequences was subtracted by modified itself and amplified with B-specific primer (lane 6), the second strand sequences was subtracted by modified itself and amplified with A-specific primer (lane 7), the first strand sequences was subtracted by modified second strand sequences and amplified with B-specific primer (lane 8), and the second strand sequences was subtracted by modified first strand sequences and amplified with A-specific primer (lane 9). Herein said first strand sequences are those nucleotide sequences with B-specific primer and said second strand sequences are those nucleotide sequences with A-specific primer. Therefore, based on the result of FIG. 2, the present invention is so sensitive and specific that all homologues between two strands of nucleotide sequences can be covalently subtracted even after PCR amplification.

The present invention has been described with reference to particular preferred embodiments; however, the scope of this invention is defined by the attached claims and should be constructed to include reasonable equivalents.

Defined in detail, the present invention is a method of performing improved directly covalent bond formation between interstrand nucleotides, comprising the steps of:

a. providing a first strand of nucleotide sequences, wherein said first strand of nucleotide sequences is not modified by amino-blocking agent in order to preserve activating amino-groups on its nucleotide base structure(s);

b. contacting said first strand of nucleotide sequences in denatured form with a second strand of denatured nucleotide sequences, wherein said second strand of denatured nucleotide sequences is single-stranded by amino-blocking agent and then modified by carboxylating conditions in its nucleotide base structure(s), to form a denatured mixture;

c. permitting said first strand and said second strand of nucleotide sequences in said denatured mixture to form double-stranded hybrid duplexes comprising covalent bonding between the activating amino-groups of said first strand and the modified carboxyl-groups of said second strand of nucleotide sequences; and d. whereby said method provides a fast, simple, specific and direct covalent bond formation between said two strands of nucleotide sequences.

Alternatively defined in detail, the present invention is a kit for performing improved directly covalent bond formation between interstrand nucleotides, comprising:

a. an amino-blocking agent which makes said second strand of nucleotide sequences single-stranded;

b. a carboxylating agent which generates carboxyl-groups on the nucleotide base of said second strand of nucleotide sequences;

c. a hybridization buffer which permits said first strand and said second strand of nucleotide sequences in a denatured mixture to form directly covalent-bonded hybrid duplexes; and d. whereby said kit can be used to provide a fast, simple, specific and direct covalent bond formation between said two strands of nucleotide sequences.

Defined broadly, the present invention is a method of performing improved directly covalent bond formation between interstrand nucleotides, comprising the steps of:

a. providing a first strand of nucleotide sequences, wherein said first strand of nucleotide sequences is not modified by redox modification reagents in order to preserve activating groups on its nucleotide base structure;

b. contacting said first strand of nucleotide sequences in denatured form with a second strand of denatured nucleotide sequences, wherein said second strand of nucleotide sequences is single-stranded and covalently modified by said redox modification reagents in its nucleotide base structure, to form a denatured mixture;

c. permitting said first strand and said second strand of nucleotide sequences in said denatured mixture to form covalently bonded hybrid duplexes between the activating groups of said first strand and the modified groups of said second strand of nucleotide sequences; and d. whereby said method provides a fast, simple, specific and direct covalent bond formation between said two strands of nucleotide sequences.

Attentively defined broadly, the present invention is a kit for performing improved directly covalent bond formation between interstrand nucleotides, comprising:

a. a set of redox modification reagents which make said second strand of nucleotide sequences single-stranded and modified for covalently bonding with said first strand of nucleotide sequences;

b. a hybridization buffer which permits said first strand and said second strand of nucleotide sequences in a denatured mixture to form directly covalent-bonded hybrid duplexes; and c. whereby said kit can be used to provide a fast, simple, specific and direct covalent bond formation between said two strands of nucleotide sequences.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to shown all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A method of performing improved directly covalent bond formation between interstrand nucleotides, comprising the steps of:
   a. providing a first strand of nucleotide sequences, wherein said first strand of nucleotide sequences is not modified by amino-blocking agent in order to preserve activating amino-groups on its nucleotide base structure;
   b. contacting said first strand of nucleotide sequences in denatured form with a second strand of denatured nucleotide sequences, wherein said second strand of denatured nucleotide sequences is single-stranded by amino-blocking agent and then modified by carboxylating conditions in its nucleotide base structure, to form a denatured mixture;
   c. permitting said first strand and said second strand of nucleotide sequences in said denatured mixture to form double-stranded hybrid duplexes comprising covalent bonding between the activating amino-groups of said first strand and the modified carboxyl-groups of said second strand of nucleotide sequences; and
   d. whereby said method provides a directly covalent bond formation between said two strands of nucleotide sequences.

2. The method as defined in claim 1, further comprising the step of repeating steps (b) through (c) on said hybrid duplexes at least one time.

3. The method as defined in claim 1, further comprising the step of nucleotide-analog incorporation into said second strand of nucleotide sequences between step (a) and step (b).

4. The method as defined in claim 3, wherein said nucleotide analogs are incorporated into said second strand of nucleotide sequences by DNA polymerase.

5. The method as defined in claim 4, wherein said nucleotide analogs are deoxyuridine triphosphate derivatives.

6. The method as defined in claim 1, wherein said second strand of nucleotide sequences is single-stranded by said amino-blocking agent and then modified by said carboxylating conditions in order to generate carboxyl-groups on its nucleotide base structure.

7. The method as defined in claim 6, wherein said amino-blocking agent is an acetic anhydride reagent.

8. The method as defined in claim 6, wherein said amino-blocking agent is an acetyl chloride reagent.

9. The method as defined in claim 6, wherein said carboxylating conditions are potassium permanganate containing reagents.

10. The method as defined in claim 1, wherein said double-stranded hybrid duplexes are homologues from complementary sequences of said first strand and said second strand of nucleotide sequences.

11. The method as defined in claim 1, wherein said first strand and said second strand of nucleotide sequences have a ratio of between about $1:1^+$ and about 1:100.

12. The method as defined in claim 11, wherein said ratio is about 1:5 to about 1:10.

13. A kit for performing improved directly covalent bond formation between interstrand nucleotides, comprising:
   a. an amino-blocking agent which makes said second strand of nucleotide sequences single-stranded;
   b. a carboxylating condition which generates carboxyl-groups on the nucleotide base of said second strand of nucleotide sequences;
   c. a hybridization buffer which permits said first strand and said second strand of nucleotide sequences in a denatured mixture to form directly covalent-bonded hybrid duplexes; and d. whereby said kit can be used to provide a directly covalent bond formation between said two strands of nucleotide sequences.

14. The kit as defined in claim 13, further comprising nucleotide analogs for incorporating into said second strand of nucleotide sequences.

15. The kit as defined in claim 14, wherein said nucleotide analogs are deoxyuridine triphosphate derivatives.

16. The kit as defined in claim 14, wherein said nucleotide analogs are incorporated into said second strand of nucleotide sequences by DNA polymerase.

17. The kit as defined in claim 16, wherein said DNA polymerase is Taq polymerase.

18. The kit as defined in claim 16, wherein said DNA polymerase is E. coli DNA polymerase 1 which contains Klenow fragment activity.

19. The kit as defined in claim 13, wherein said amino-blocking agent is an acetic anhydride reagent.

20. The kit as defined in claim 13, wherein said amino-blocking agent is an acetyl chloride reagent.

21. The kit as defined in claim 13, wherein said carboxylating condition is a potassium permanganate reagent.

22. The kit as defined in claim 13, wherein said hybridization buffer is N-[2-hydroxyethyl]piperazine-N'-[3-propanesulfonic acid] and [ethylenedinitrilo]tetraacetic acid mixture buffer.

23. The kit as defined in claim 13, wherein said hybridization buffer is N-[2-hydroxyethyl]piperazine-N'-[2-ethopanesulfonic acid] [ethylenedinitrilo]tetraacetic acid and sodium dodecyl sulfate mixture buffer.

24. The kit as defined in claim 13, wherein said first strand and said second strand of nucleotide sequences have a ratio of between about $1:1^+$ and about 1:100.

25. The kit as defined in claim 24, wherein said ratio is about 1:5 to about 1:10.

26. A method of performing improved directly covalent bond formation between interstrand nucleotides, comprising the steps of:

a. providing a first strand of nucleotide sequences, wherein said first strand of nucleotide sequences is not modified by redox modification reagents in order to preserve activating groups on its nucleotide base structure;

b. contacting said first strand of nucleotide sequences in denatured form with a second strand of denatured nucleotide sequences, wherein said second strand of nucleotide sequences is single-stranded and covalently modified by said redox modification reagents in its nucleotide base structure, to form a denatured mixture;

c. permitting said first strand and said second strand of nucleotide sequences in said denatured mixture to condense into covalently bonded hybrid duplexes between the activating groups of said first strand and the modified groups of said second strand of nucleotide sequences; and d. whereby said method provides a directly covalent bond formation between said two strands of nucleotide sequences.

27. The method as defined in claim 26, further comprising the step of repeating steps (b) through (c) on said hybrid duplexes at least one time.

28. The method as defined in claim 26, further comprising the step of nucleotide-analog incorporation into said second strand of nucleotide sequences between step (a) and step (b).

29. The method as defined in claim 28, wherein said nucleotide analogs are incorporated into said second strand of nucleotide sequences by DNA polymerase.

30. The method as defined in claim 28, wherein said nucleotide analogs are deoxyuridine triphosphate derivatives.

31. The method as defined in claim 26, wherein said second strand of nucleotide sequences is single-stranded and modified by said chemical reagents in order to generate modified interacting groups for covalently bonding with said activating groups of said first strand of nucleotide sequences.

32. The method as defined in claim 31, wherein said redox modification reagents contain acetic anhydride.

33. The method as defined in claim 31, wherein said redox modification reagents contain alkaline acetic chloride.

34. The method as defined in claim 31, wherein said redox modification reagents contain alkaline potassium permanganate.

35. The method as defined in claim 26, wherein said covalently bonded hybrid duplexes are homologues from complementary sequences of said first strand and said second strand of nucleotide sequences.

36. The method as defined in claim 26, wherein said first strand and said second strand of nucleotide sequences have a ratio of between about $1:1^+$ and about 1:100.

37. The method as defined in claim 36, wherein said ratio is about 1:5 to about 1:10.

38. A kit for performing improved directly covalent bond formation between interstrand nucleotides, comprising:

a. a set of redox modification reagents which make said second strand of nucleotide sequences single-stranded and modified for covalently bonding with said first strand of nucleotide sequences;

b. a hybridization buffer which condenses said first strand and said second strand of nucleotide sequences in a denatured mixture to form directly covalent-bonded hybrid duplexes; and c. whereby said kit can be used to provide a directly covalent bond formation between said two strands of nucleotide sequences.

39. The kit as defined in claim 38, further comprising nucleotide analogs for incorporating into said second strand of nucleotide sequences.

40. The kit as defined in claim 39, wherein said nucleotide analogs are deoxyuridine triphosphate derivatives.

41. The kit as defined in claim 39, wherein said nucleotide analogs are incorporated into said second strand of nucleotide sequences by DNA polymerase.

42. The kit as defined in claim 41, wherein said DNA polymerase is Taq polymerase.

43. The kit as defined in claim 41, wherein said DNA polymerase is E. coli DNA polymerase 1 which contains Klenow fragment activity.

44. The kit as defined in claim 38, wherein said redox modification reagents are acetic anhydride reagent and alkaline potassium permanganate reagent.

45. The kit as defined in claim 38, wherein said redox modification reagents are alkaline acetic chloride reagent and alkaline potassium permanganate reagent.

46. The kit as defined in claim 38, wherein said hybridization buffer is a N,N'-diisopropylcarbodiimide, N-[2-hydroxyethyl]piperazine-N'-[3-propanesulfonic acid] and [ethylenedinitrilo]tetraacetic acid mixture buffer.

47. The kit as defined in claim 38, wherein said hybridization buffer is a N,N'-dicyclohaxylcarbodiimide, N-[2-hydroxyethyl]piperazine-N'-[2-ethanesulfonic acid], [ethylenedinitrilo]tetraacetic acid and sodium dodecyl sulfate mixture buffer.

48. The kit as defined in claim 38, wherein said first strand and said second strand of nucleotide sequences have a ratio of between about $1:1^+$ and about 1: 100.

49. The kit as defined in claim 48, wherein said ratio is about 1:5 to about 1:10.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:1:

GCCACCAGAA GAGCGTGTAC GTCC                                              24

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Synthetic DNA"

(xi) SEQUENCE DESCRIPTION: SEQ ID NO:2:

CGGTAGTGAC TCGGTTAAGA TCGC                                              24